United States Patent
Guida et al.

(10) Patent No.: US 11,922,629 B2
(45) Date of Patent: Mar. 5, 2024

(54) SYSTEMS AND METHODS FOR GENERATING CANCER PREDICTION MAPS FROM MULTIPARAMETRIC MAGNETIC RESONANCE IMAGES USING DEEP LEARNING

(71) Applicant: NOVA SCOTIA HEALTH AUTHORITY, Halifax (CA)

(72) Inventors: Alessandro Guida, Avonport (CA); David Hoar, Hammonds Plains (CA); Peter Lee, Bedford (CA); Steve Patterson, Halifax (CA); Sharon Clarke, Halifax (CA); Chris Bowen, Halifax (CA)

(73) Assignee: NOVA SCOTIA HEALTH AUTHORITY, Halifax (CA)

(*) Notice: Subject to any disclaimer, the term of this patent is extended or adjusted under 35 U.S.C. 154(b) by 205 days.

(21) Appl. No.: 17/416,734

(22) PCT Filed: Dec. 11, 2019

(86) PCT No.: PCT/CA2019/051788
§ 371 (c)(1),
(2) Date: Jun. 21, 2021

(87) PCT Pub. No.: WO2020/124208
PCT Pub. Date: Jun. 25, 2020

(65) Prior Publication Data
US 2022/0076422 A1    Mar. 10, 2022

Related U.S. Application Data

(60) Provisional application No. 62/783,734, filed on Dec. 21, 2018.

(51) Int. Cl.
G06T 7/00 (2017.01)
G06N 3/045 (2023.01)
G06T 7/11 (2017.01)

(52) U.S. Cl.
CPC ............. G06T 7/11 (2017.01); G06N 3/045 (2023.01); G06T 2207/10088 (2013.01);
(Continued)

(58) Field of Classification Search
CPC ............ G06T 7/11; G06T 2207/10088; G06T 2207/20081; G06T 2207/20084;
(Continued)

(56) References Cited

U.S. PATENT DOCUMENTS 9,858,665 B2 * 1/2018 Metzger ............... G06T 7/0012
10,388,017 B2 * 8/2019 Jacobs .................. A61B 5/055
(Continued)

FOREIGN PATENT DOCUMENTS

CN    106683104 A    5/2017
CN    107240102 A    10/2017
(Continued)

OTHER PUBLICATIONS

Abadi, Martin, Ashish Agarwal, Paul Barham, Eugene Brevdo, Zhifeng Chen, Craig Citro, Greg S. Corrado, et al., 2016, "TensorFlow: Large-Scale Machine Learning on Heterogeneous Distributed Systems", arXiv [cs.DC], arXiv, http://arxiv.org/abs/1603.04467, 19 pages.

(Continued)

Primary Examiner — Van D Huynh
(74) Attorney, Agent, or Firm — HILL & SCHUMACHER (57) ABSTRACT

Various example embodiments are described in which an anisotropic encoder-decoder convolutional neural network architecture is employed to process multiparametric mag- (Continued)

netic resonance images for the generation of cancer predication maps. In some example embodiments, a simplified anisotropic encoder-decoder convolutional neural network architecture may include an encoder portion that is deeper than a decoder portion. In some example embodiments, simplified network architectures may be combined with test-time-augmentation in order to facilitate training and testing with a minimal number of test subjects.

21 Claims, 6 Drawing Sheets

(52) U.S. Cl.
CPC .............. *G06T 2207/20081* (2013.01); *G06T 2207/20084* (2013.01); *G06T 2207/30096* (2013.01)

(58) Field of Classification Search
CPC .......... G06T 2207/30096; G06N 3/045; G06N 3/08; G01R 33/5608; A61B 5/055; G16H 30/40; G16H 50/20
USPC ......................................................... 382/128
See application file for complete search history.

(56) References Cited

U.S. PATENT DOCUMENTS

| | | | |
|---|---|---|---|
| 2017/0371017 A1* | 12/2017 | Odry | G01R 33/5602 |
| 2018/0240233 A1* | 8/2018 | Kiraly | G06T 7/0012 |
| 2020/0020082 A1* | 1/2020 | Zahneisen | G06T 7/0012 |
| 2020/0058126 A1* | 2/2020 | Wang | G06F 18/213 |
| 2020/0167930 A1* | 5/2020 | Wang | G06N 3/08 |
| 2020/0286232 A1* | 9/2020 | Enzmann | G06T 7/143 |
| 2020/0342359 A1* | 10/2020 | Hu | G06N 20/10 |

FOREIGN PATENT DOCUMENTS

| | | |
|---|---|---|
| CN | 107886510 A | 4/2018 |
| WO | 2017165801 A1 | 9/2017 |

OTHER PUBLICATIONS

Deng, J., W. Dong, R. Socher, L. Li, Kai Li, and Li Fei-Fei, 2009, "ImageNet: A Large-Scale Hierarchical Image Database," In 2009 IEEE Conference on Computer Vision and Pattern Recognition , 248-55.

Dieleman, Sander, Jeffrey De Fauw, and Koray Kavukcuoglu, 2016, "Exploiting Cyclic Symmetry in Convolutional Neural Networks." arXiv [cs.LG]. arXiv. http://arxiv.org/abs/1602.02660, 10 pages.

Dumoulin, Vincent, and Francesco Visin,2016, "A Guide to Convolution Arithmetic for Deep Learning", arXiv [stat.ML]. arXiv. http://arxiv.org/abs/1603.07285, 31 pages.

Garcia-Reyes, Kirema, Niccolò M. Passoni, Mark L. Palmeri, Christopher R. Kauffman, Kingshuk Roy Choudhury, Thomas J. Polascik, and Rajan T. Gupta, 2015, "Detection of Prostate Cancer with Multiparametric MRI (mpMRI): Effect of Dedicated Reader Education on Accuracy and Confidence of Index and Anterior Cancer Diagnosis," Abdominal Imaging 40 (1): 134-42.

Giannini, Valentina, Simone Mazzetti, Enrico Armando, Silvia Carabalona, Filippo Russo, Alessandro Giacobbe, Giovanni Muto, and Daniele Regge, 2017, "Multiparametric Magnetic Resonance Imaging of the Prostate with Computer-Aided Detection: Experienced Observer Performance Study," European Radiology 27 (10): 4200-4208.

Hambrock, Thomas, and B. MBCh, 2013, "Prostate Cancer: Computer-Aided Diagnosis with Multiparametric 3-T MR Imaging—Effect on Observer Performance1," Radiology 266 (2), https://doi.org/ 10.1148/radiol.12111634/-/DC1, 10 pages.

He, Kaiming, Xiangyu Zhang, Shaoqing Ren, and Jian Sun. 2015, "Deep Residual Learning for Image Recognition." arXiv [cs.CV]. arXiv, http://arxiv.org/abs/1512.03385, 12 pages.

Hua, Kai-Lung, Che-Hao Hsu, Shintami Chusnul Hidayati, Wen-Huang Cheng, and Yu-Jen Chen. 2015. "Computer-Aided Classification of Lung Nodules on Computed Tomography Images via Deep Learning Technique." OncoTargets and Therapy 8 (August): 2015-22, 8 pages.

Kingma, Diederik P., and Jimmy Ba. 2014. "Adam: A Method for Stochastic Optimization." arXiv [cs.LG]. arXiv. http://arxiv.org/abs/1412.6980, 15 pages.

Lakhani, Paras, and Baskaran Sundaram. 2017. "Deep Learning at Chest Radiography: Automated Classification of Pulmonary Tuberculosis by Using Convolutional Neural Networks." Radiology 284 (2): 574-82.

Le, Minh Hung, Jingyu Chen, Liang Wang, Zhiwei Wang, Wenyu Liu, Kwang-Ting Tim Cheng, and Xin Yang. 2017. "Automated Diagnosis of Prostate Cancer in Multi-Parametric MRI Based on Multimodal Convolutional Neural Networks." Physics in Medicine and Biology 62 (16): 6497-6514.

Milletari, F., N. Navab, and S. Ahmadi. 2016. "V-Net: Fully Convolutional Neural Networks for Volumetric Medical Image Segmentation." In 2016 Fourth International Conference on 3D Vision (3DV) , 565-71.

Muller, Berrend G., Joanna H. Shih, Sandeep Sankineni, Jamie Marko, Soroush Rais-Bahrami, Arvin Koruthu George, Jean J. M. C. H. de la Rosette, et al. 2015. "Prostate Cancer: Interobserver Agreement and Accuracy with the Revised Prostate Imaging Reporting and Data System at Multiparametric MR Imaging." Radiology 277 (3): 741-50.

Pereira, Sergio, Adriano Pinto, Victor Alves, and Carlos A. Silva. 2016. "Brain Tumor Segmentation Using Convolutional Neural Networks in MRI Images." IEEE Transactions on Medical Imaging 35 (5): 1240-51.

Roehrborn, Claus G., and Libby K. Black. 2011. "The Economic Burden of Prostate Cancer." BJU International 108 (6): 806-13, 9 pages.

Rosenkrantz, Andrew B., Luke A. Ginocchio, Daniel Comfeld, Adam T. Froemming, Rajan T. Gupta, Baris Turkbey, Antonio C. Westphalen, James S. Babb, and Daniel J. Margolis. 2016. "Interobserver Reproducibility of the PI-RADS Version 2 Lexicon: A Multicenter Study of Six Experienced Prostate Radiologists." Radiology 280 (3): 793-804.

Sanyal, C., A. G. Aprikian, S. Chevalier, F. L. Cury, and A. Dragomir. 2013. "Direct Cost for Initial Management of Prostate Cancer: A Systematic Review." Current Oncology 20 (6): e522-31.

Sermanet, Pierre, David Eigen, Xiang Zhang, Michael Mathieu, Rob Fergus, and Yann LeCun. 2013. "OverFeat: Integrated Recognition, Localization and Detection Using Convolutional Networks." arXiv [cs.CV]. arXiv. http://arxiv.org/abs/1312.6229, 16 pages.

Shelhamer, Evan, Jonathan Long, and Trevor Darrell. 2017. "Fully Convolutional Networks for Semantic Segmentation." IEEE Transactions on Pattern Analysis and Machine Intelligence 39 (4): 640-51.

Shi, Wenzhe, Jose Caballero, Lucas Theis, Ferenc Huszar, Andrew Aitken, Christian Ledig, and Zehan Wang. 2016. "Is the Deconvolution Layer the Same as a Convolutional Layer?" arXiv [cs.CV]. arXiv. http://arxiv.org/abs/1609.07009, 7 pages.

Simonyan, Karen, and Andrew Zisserman. 2014. "Very Deep Convolutional Networks for Large-Scale Image Recognition." arXiv [cs.CV]. arXiv. http://arxiv.org/abs/1409.1556, 14 pages.

Torre, Lindsey A., Freddie Bray, Rebecca L. Siegel, Jacques Ferlay, Joannie Lortet-Tieulent, and Ahmedin Jemal. 2015. "Global Cancer Statistics, 2012." CA: A Cancer Journal for Clinicians 65 (2): 87-108.

Weinreb, Jeffrey C., Jelle O. Barentsz, Peter L. Choyke, Francois Cornud, Masoom A. Haider, Katarzyna J. Macura, Daniel Margolis, et al. 2016. "PI-RADS Prostate Imaging—Reporting and Data System: 2015, Version 2." European Urology 69 (1): 16-40.

Yang, Xin, Chaoyue Liu, Zhiwei Wang, Jun Yang, Hung Le Min, Liang Wang, and Kwang-Ting Tim Cheng. 2017. "Co-Trained (56) References Cited

OTHER PUBLICATIONS

Convolutional Neural Networks for Automated Detection of Prostate Cancer in Multi-Parametric MRI." Medical Image Analysis 42 (December): 212-27.
Yosinski, Jason, Jeff Clune, Yoshua Bengio, and Hod Lipson. 2014. "How Transferable Are Features in Deep Neural Networks?" In Advances in Neural Information Processing Systems 27, edited by Z. Ghahramani, M. Welling, C. Cortes, N. D. Lawrence, and K. Q. Weinberger, 3320-28. Curran Associates, Inc.
Jia, H. et al., "3D Global Convolutional Adversarial network for Prostate mR Volume Segmentation", arXiv:1807.06742, 1-9, 2018.
Tian, Z. et al., "Deep convolutional neural network for prostate MR segmentation", Int. J. Comput. Assist. Radiol. Surg. 13, 1687-1696, 2018.
Song, Y. et al., "Computer-Aided Diagnosis of Prostate Cancerl Using a Deep Convolutional Neural Network from Multiparametric MRI", J. Magn. Reson. Imaging 48, 1570-1577, 2018.
Liu, S. et al., "Prostate Cancer Diagnosis using Deep Learning with 3D Multiparametric MRI", arXiv:1703.04078, 1-4, 2017.
International search report PCT/CA2019/051788 dated Apr. 28, 2020, 3 pages.
S. M. Kamrul Hasan and C. A. Linte, "A Modified U-Net Convolutional Network Featuring a Nearest-neighbor Re-sampling-based Elastic-Transformation for Brain Tissue Characterization and Segmentation," 2018 IEEE Western New York Image and Signal Processing Workshop (WNYISPW), Rochester, NY, 2018, pp. 1-5.
S. Hussain, S. M. Anwar and M. Majid, "Brain tumor segmentation using cascaded deep convolutional neural network," 2017 39th Annual International Conference of the IEEE Engineering in Medicine and Biology Society (EMBC), Seogwipo, 2017, pp. 1998-2001.

\* cited by examiner

| transformation | parameter range | Number of images |
|---|---|---|
| scaling | 0.90 to 1.00 | 5 |
| rotation | 6.0° to -6.0° | 5 |
| flipping | sagittal plane | 5 |

SYSTEMS AND METHODS FOR GENERATING CANCER PREDICTION MAPS FROM MULTIPARAMETRIC MAGNETIC RESONANCE IMAGES USING DEEP LEARNING

CROSS-REFERENCE TO RELATED APPLICATION

This application is a National Phase application claiming the benefit of the international PCT Patent Application No. PCT/CA2019/051788, filed on Dec. 11, 2019, in English, which claims priority to U.S. Provisional Patent Application No. 62/783,734, titled "SYSTEMS AND METHODS FOR GENERATING CANCER PREDICTION MAPS FROM MULTIPARAMETRIC MAGNETIC RESONANCE IMAGES USING DEEP LEARNING" and filed on Dec. 21, 2018, the entire contents of which are incorporated herein by reference.

BACKGROUND

The present disclosure relates to the detection and classification of cancer in medical images. More particularly, the present disclosure relates to automated cancer segmentation from multiparametric MR images.

Prostate cancer was the second most frequently diagnosed cancer in men and the fifth leading cause of cancer death worldwide in 2012 (Torre et al. 2015). The incidence in developed countries is on the rise and is associated with a significant socioeconomic burden (Roehrborn and Black 2011; Sanyal et al. 2013). Evaluation of a patient suspected of having prostate cancer most commonly involves systematic random transrectal ultrasound-guided (TRUS) core biopsy. This approach, however, has several known limitations including failure to sample clinically significant cancer and under estimation of Gleason score. Due to these disadvantages, there is increasing interest in prostate cancer detection and staging with multiparametric MRI. In 2014, the National Institute of Clinical Excellence guidelines for prostate cancer management were modified to include consideration of multiparametric magnetic resonance imaging (MRI) after a negative TRUS biopsy to determine if another biopsy is needed, and in men with histologically proven cancer when changes in tumor (T) or nodal (N) stage would alter management.

The Prostate Imaging Reporting and Data System (PI-RADS) recommends that the multiparametric MRI examination consist of tri-planar T2 weighted (T2w), diffusion weighted imaging (DWI) with associated apparent diffusion coefficient (ADC) map, and dynamic contrast enhanced (DCE) sequences; the DCE series should image the prostate for 3-5 minutes post-contrast administration with a temporal resolution of <7 seconds per volume (Weinreb et al. 2016). Thus, the multiparametric MRI examination generates hundreds, if not thousands, of images for radiologic review. Consequently, interpretation is time consuming and diagnostic accuracy is dependent upon the expertise of the reporting radiologist (Garcia-Reyes et al. 2015). Although PI-RADS provides a standardized lexicon for interpreting and reporting multiparametric MRI, there remains considerable inter-observer variability (Rosenkrantz et al. 2016; Muller et al. 2015).

Machine learning has the potential to reliably and objectively integrate a large amount of MRI data to create a map of cancer probability. When used as a diagnostic aid by the radiologist, such an approach has been shown to increase efficiency and accuracy while reducing inter-variability (Hambrock and MBCh 2013; Giannini et al. 2017).

SUMMARY

Various example embodiments are described in which an anisotropic encoder-decoder convolutional neural network architecture is employed to process multiparametric magnetic resonance images for the generation of cancer predication maps. In some example embodiments, a simplified anisotropic encoder-decoder convolutional neural network architecture may include an encoder portion that is deeper than a decoder portion. In some example embodiments, simplified network architectures may be combined with test-time-augmentation in order to facilitate training and testing with a minimal number of test subjects.

Accordingly, in a first aspect, there is provided a method of implementing a convolutional neural network for generating cancer prediction maps based on processing of multiparametric magnetic resonance images, the method comprising:

defining an anisotropic encoder-decoder convolutional neural network for processing multiparametric magnetic resonance images, wherein the anisotropic encoder-decoder convolutional neural network is configured such that an output thereof is a pixelated prediction image map, with each pixel of the pixelated prediction image map configured to provide a binary determination of a presence or absence of cancer;

performing supervised transfer learning to pretrain the anisotropic encoder-decoder convolutional neural network;

training the anisotropic encoder-decoder convolutional neural network with a plurality of multiparametric magnetic resonance training image sets and respective ground truth training image sets, each multiparametric magnetic resonance training image set corresponding to a given subject and comprising a plurality of multiparametric magnetic resonance image slices; and employing test-time-augmentation to test the anisotropic encoder-decoder convolutional neural network with a plurality of multiparametric magnetic resonance test image sets and respective ground truth test image sets;

wherein test-time-augmentation is performed, when processing a given slice of a multiparametric magnetic resonance test image set, according to the steps of:

applying a plurality of transformations to the multiparametric magnetic resonance images corresponding to the given slice, thereby obtaining a plurality of transformed multiparametric magnetic resonance images;

employing the anisotropic encoder-decoder convolutional neural network to generate, for each transformed multiparametric magnetic resonance image, an intermediate cancer prediction map;

rectifying each intermediate cancer prediction map by applying a respective inverse transformation, thereby obtaining a plurality of rectified intermediate cancer prediction maps; and combining the plurality of rectified intermediate cancer prediction maps to generate a composite cancer prediction map.

In another aspect, there is provided a method of employing an anisotropic encoder-decoder convolution neural network to generate cancer prediction maps based on processing of a multiparametric magnetic resonance image set associated with a subject, the anisotropic encoder-decoder convolution neural network anisotropic encoder-decoder convolutional neural network being configured such that an output thereof is a pixelated prediction image map, with each pixel of the pixelated prediction image map configured to provide a binary determination of a presence or absence of cancer;

the method comprising employing test-time-augmentation to process the multiparametric magnetic resonance image set via the anisotropic encoder-decoder convolutional neural network;

wherein test-time-augmentation is performed, when processing a given slice of the multiparametric magnetic resonance image set, according to the steps of:

applying a plurality of transformations to the multiparametric magnetic resonance images corresponding to the given slice, thereby obtaining a plurality of transformed multiparametric magnetic resonance images;

employing the anisotropic encoder-decoder convolutional neural network to generate, for each transformed multiparametric magnetic resonance image, an intermediate cancer prediction map;

rectifying each intermediate cancer prediction map by applying a respective inverse transformation, thereby obtaining a plurality of rectified intermediate cancer prediction maps; and combining the plurality of rectified intermediate cancer prediction maps to generate a composite cancer prediction map.

In another aspect, there is provided a system for processing multiparametric magnetic resonance images for cancer segmentation, the system comprising:

processing circuitry comprising at least one processor and associated memory, wherein the memory stores instructions executable by the at least one processor for performing operations comprising:

employing test-time-augmentation to process a multiparametric magnetic resonance image set via an anisotropic encoder-decoder convolutional neural network, the anisotropic encoder-decoder convolution neural network anisotropic encoder-decoder convolutional neural network being configured such that an output thereof is a pixelated prediction image map, with each pixel of the pixelated prediction image map configured to provide a binary determination of a presence or absence of cancer;

wherein test-time-augmentation is performed, when processing a given slice of the multiparametric magnetic resonance image set, according to the steps of:

applying a plurality of transformations to the multiparametric magnetic resonance images corresponding to the given slice, thereby obtaining a plurality of transformed multiparametric magnetic resonance images;

employing the anisotropic encoder-decoder convolutional neural network to generate, for each transformed multiparametric magnetic resonance image, an intermediate cancer prediction map;

rectifying each intermediate cancer prediction map by applying a respective inverse transformation, thereby obtaining a plurality of rectified intermediate cancer prediction maps; and combining the plurality of rectified intermediate cancer prediction maps to generate a composite cancer prediction map.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 6A-6E show a series of prostate images and associated cancer prediction maps. FIG. 6A shows an original prostate image from the first subject, slice 18 and FIG. 6E shows an image from second subject slice 13, both shown using channel T2w. Voxel values of the regions outside the prostate are set to 0. FIGS. 6B and 6F show the cancer segmentation using a Logistic Regression classifier; FIGS. 6C and 6G show the cancer segmentation using a Random Forest classifier; and FIGS. 6D and 6H show results from the CNN model with TTA and supervised transfer learning. Dark gray areas indicate non-cancer predicted pixels while light gray areas indicate cancer predictions.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

The present inventors, when considering the feasibility of employing convolutional neural networks for cancer prediction based on multiparametric MR images, recognized that previous approaches suffered from two key problems. Firstly, previous approaches to cancer prediction typically focused on a simple classification problem—i.e. a single global binary classification outcome (namely cancer versus non-cancer) associated with an image or image set or a simple localization prediction with bounding boxes (Sermanet et al. 2013). The present inventors recognized that such approaches are limited in their clinical utility as they fail to provide sufficient spatial discrimination in cancer assessment. In order to address this shortcoming, the present inventors sought to develop a convolutional neural network architecture and associated processing workflow that would provide classification on a per-pixel basis—i.e. an architecture and associated workflow that would facilitate the generation of a cancer prediction map (e.g. a heat map) with cancer vs. noncancer classification at the pixel level. Such a classifier, capable of additionally providing location and classification information with pixel-wise resolution, could result in a powerful aid to the clinician.

The present inventors realized, however, that conventional convolutional neural network architectures, such as those based on fully-connected layers, would be difficult to train and test with the limited amount of ground truth clinical data that is typically accessible in biomedical imaging applications. To address this need, various example embodiments are described below in which a simplified encoder-decoder convolutional neural network architecture is employed in order to facilitate training and testing with a limited number of subjects. As described below, in some example embodiments, a simplified encoder-decoder convolutional neural network having an anisotropic architecture with an encoder portion that is deeper than a decoder portion, is combined with test time augmentation in order to facilitate testing with a minimal number of test subjects.

Figure 1:
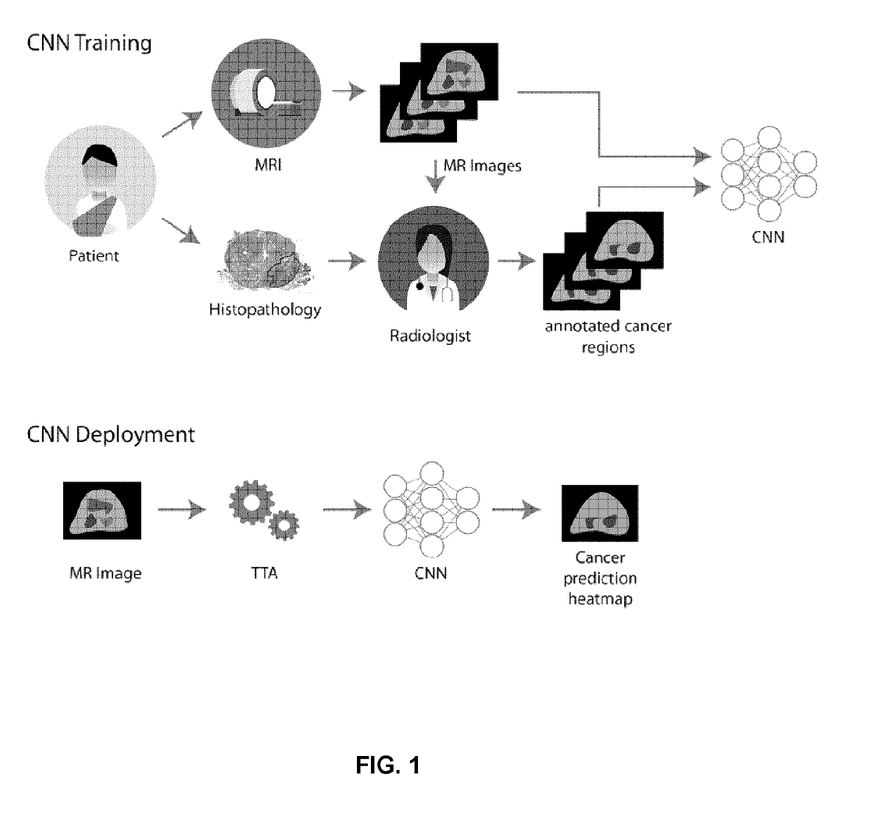
FIG. 1 shows a schematic of an example workflow for training and deploying a convolutional neural network for cancer detection from multiparametric MR images.

Referring now to FIG. 1A, and example workflow is shown for the training and implementation of a convolutional neural network for the automated analysis of multiparametric MR images. The example workflow involves includes training-set labelling, image pre-processing, model training, and subsequent model test and deployment.

Training set labelling is performed prior to model training and involves the adjudication of clinical samples that correspond to multiparametric MR training images, thereby providing the ground truths associated with training and testing data. In the example workflow shown in FIG. 1, training set labelling involves performing histopathology to obtain histopathology samples corresponding to training image set and employing a radiologist (preferably blinded to the MR image data) to identify and annotate tumor regions. It will be understood that histopathology-based labelling is but one example method of performing training set labelling.

As shown in FIG. 1A, multiparametric MR training images (e.g. T2w, ADC, Ktrans) may be preprocessed prior to using them for training the convolutional neural network. For example, according to one example implementation, each of the multiparametric MR images may be individually cropped around a region of interest (ROI) mask of the relevant anatomy (e.g. the prostate) to minimize the number of non-prostate voxels in the images while maintaining a rectangular image. According to such an example embodiment, voxels outside of the region of interest are masked and ignored. The unmasked voxels may undergo further pre-processing: for example, the T2w channel may be normalized (e.g., in the case of prostate imaging, by the gluteus muscle mean value) to reduce the variance between different subjects, and a general z-score normalization may be performed on all voxels.

Although the present examples employ three types of images in a multiparametric image set, if will be understood that these examples are not intended to be limiting, and other types of images (e.g. other than T2w, ADC, Ktrans) may be employed.

The images from each subject can be represented by a series of s slices, (e.g. with dimensions 512×512), each having a plurality of channels c (for example, T2w, ADC, Ktrans). An input image, preprocessed as described above, may be described as a set of pixels $x \in R^{h \times w \times c}$ where h and w are the height and width of the image and c is the number of channels (i.e. MRI contrasts). The classification task may be denoted as a function that generates, for each pixel, an output $\hat{y}$ such that f: $R^{h \times w \times c} \rightarrow R^{h \times w \times c'}$. Since a segmentation task is being performed, the output image may be generated to have the same number of row and columns as the input image: m=m', n=n', thereby generating a cancer prediction map having a 1:1 pixel correspondence with the original MR images (or, in other example embodiments, pixel correspondence that maps two or more pixels to a single output pixel). In example implementations in which pixels are classified according to a binary outcome, each pixel $y \in R^{m' \times n' \times c'}$ may be labeled with either 0 or 1, where 0 identifies non-cancer pixels and 1 cancer pixels. (c'=1)

The input dataset to train and test the convolutional neural network model consist in $N_t$ images arranged in $X_{Nt} \in R^{n \times m \times c}$ and $Y_{Nt} \in R^{n \times m \times c'}$ input matrices (where c' is equal to 1). During the training phase, the convolutional neural network takes, as input, an image $X_i$ in the form of a multidimensional matrix of shape (m×n×c) and generates predictions in the form of a 2D matrix. In the present example embodiment involving binary classification on a per-pixel basis, the 2D matrix has a size of (m×n) and each voxel is a predicted class with value between 1 or 0 (cancer versus non-cancer). The prediction is then compared to the ground truth $Y_i$ and the network weights are optimized.

Figure 2:
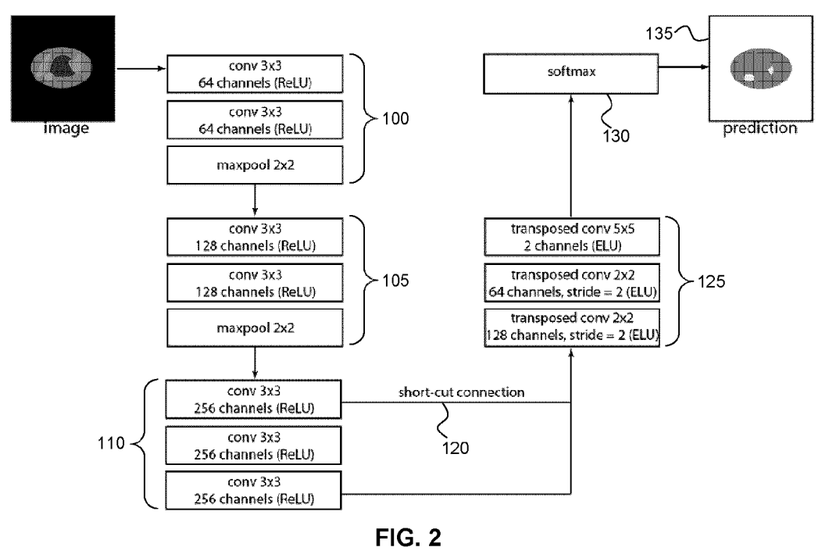
FIG. 2 is a graphical representation of an example anisotropic convolutional neural network architecture.

FIG. 2 illustrates an example of an encoder-decoder-based convolutional neural network architecture. The figure illustrates the network architecture such that the encoder portion of the network is shown in the left and the decoder portion of the network is shown on the right. The encoder portion of the network can be understood as performing the role of learning special representations of the image (the "what") while the decoder component of the network learns to map (the "where") the learned representation to the image to provide pixel-wise predictions.

The encoder portion of the network includes two or more initial convolution blocks, shown at 100 and 105 in FIG. 2, where in the present example implementation, each block includes a set convolution layers followed by a maxpool layer. The initial convolution blocks are provided such that the number of output channels increases in each initial convolution block. For example, in the non-limiting example implementation shown in FIG. 2, the example network includes two initial convolution blocks 100 and 105 having two convolution layers and a maxpool layer, where the second initial convolution block 105 employs a greater number of output channels (128) than the first initial convolution block 100 (64). The encoder portion of the network also includes a final convolution block 110 that includes a set of convolution layers having a greater number of output channels than the initial convolution blocks. For example, in the example implementation shown in FIG. 2, the final convolution block includes 256 output channels.

The decoder portion of the network is shown on the right portion of FIG. 2 and includes a deconvolution (transposed convolution) block 125 including a number of transposed convolution layers, with a decreasing output channel count per transposed convolution layer. In the example implementation shown in FIG. 2, the decoder portion of the network includes a deconvolution block having three transposed convolution layers with 128, 64 and 2 output channels, respectively.

The example architecture also includes at least one identity short-cut connection, which feeds, as input to the deconvolution block 125, summed output generated from two previous convolution layers. In the example implementation shown in FIG. 2, output from the first and final convolution layers of the final convolution block 110 are provided to the deconvolution block 125.

The output from the deconvolution block 125 is then processed by a classification layer 130 (e.g. a softmax layer), which provides binary classification (cancer vs. non-cancer) on a per-pixel level, thereby generating a cancer prediction map 135.

As can be seen from FIG. 2, the example encoder-decoder convolution neural network has an anisotropic architecture, where the encoder portion of the neural network has a different depth than the decoder portion of the neural network.

This simplicity of the example architecture shown in FIG. 2 can be important in clinical applications in which training and testing data is scarce and/or challenging to obtain. Indeed, many clinical applications, such as the example clinical application of prostate cancer detection, it can be very difficult and expensive to collect a large number of multiparametric MR image datasets due to the need to obtain histological annotated ground truth images. The resulting scarcity of data can significantly hinder the ability to properly train and/or test a convolutional neural network. In particular, if a complex convolutional neural network is trained with a small dataset (e.g. less than 100, less than 50, or less than 20 subjects, in the example case of multiparametric MR imaging, which is typical in the biomedical field), the network can be susceptible to overfitting. A simpler network, such as the example encoder-decoder networks disclosed herein and variations thereof (optionally employing test time augmentation as described below) is less subject to the risk of overfitting such a small dataset.

Indeed, while the VGG network was originally trained using 100,000 images, an example implementation of an encoder-decoder based convolutional neural network based on the architecture shown in FIG. 2 was successfully trained and tested using clinical data from only 16 subjects. This dramatic difference in the amount of training data available and necessary for training the example encoder-decoder based neural network architectures disclosed herein demonstrates the significant difference in their design and application.

It will be understood that the architecture shown in FIG. 2 is but one example of a simplified encoder-decoder convolutional neural network and that one or more aspects of the architecture may be modified without departing from the intended scope of the present disclosure. For example, while the initial convolution blocks 100 and 105 employ two convolution layers, it will be understood that the number of convolution layers is not limited to two. Also, while the convolution layers employ a kernel size of 3, it will be understood than another kernel size may be employed in the alternative.

In some example embodiments, the convolutional neural network may be pretrained. Pretraining may employ transfer learning (e.g. supervised transfer learning), which consists of training the convolutional neural network model to solve a task, known as a source task, that is related the objective task, called the target task. After the model is trained at the source task, its weights are saved and used as the initial weights during the training for the target task. Initial weights determined in this way are known to yield superior performance compared to randomly initialized weights (e.g. as described in Yosinski et al. 2014).

Figure 3A:
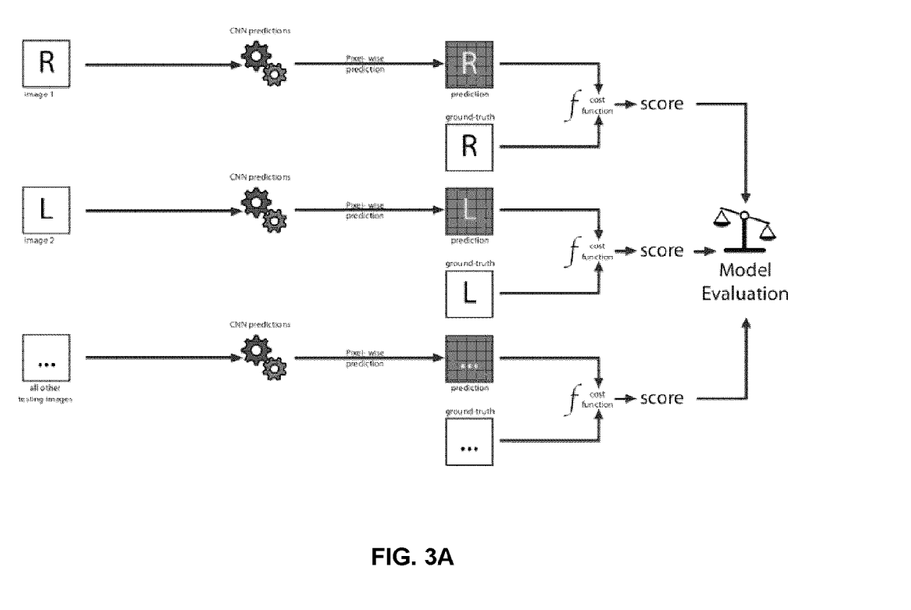
FIG. 3A illustrates a conventional convolutional neural network model evaluation workflow in the absence of test time augmentation.

As per the example embodiment described above, during the testing phase, the network takes as input an image in the form of a multidimensional matrix of shape (m×n×c) and the convolutional neural network generates a 2D matrix of size (m×n) where each pixel is a predicted class with value between 1 or 0 (cancer versus non-cancer). FIG. 3A illustrates a conventional testing workflow in which the model is evaluated during the testing phase by comparing, for multiple multiparametric MR images, the cancer prediction map generated by the convolutional neural network with the corresponding ground truth results.

Figure 3B:
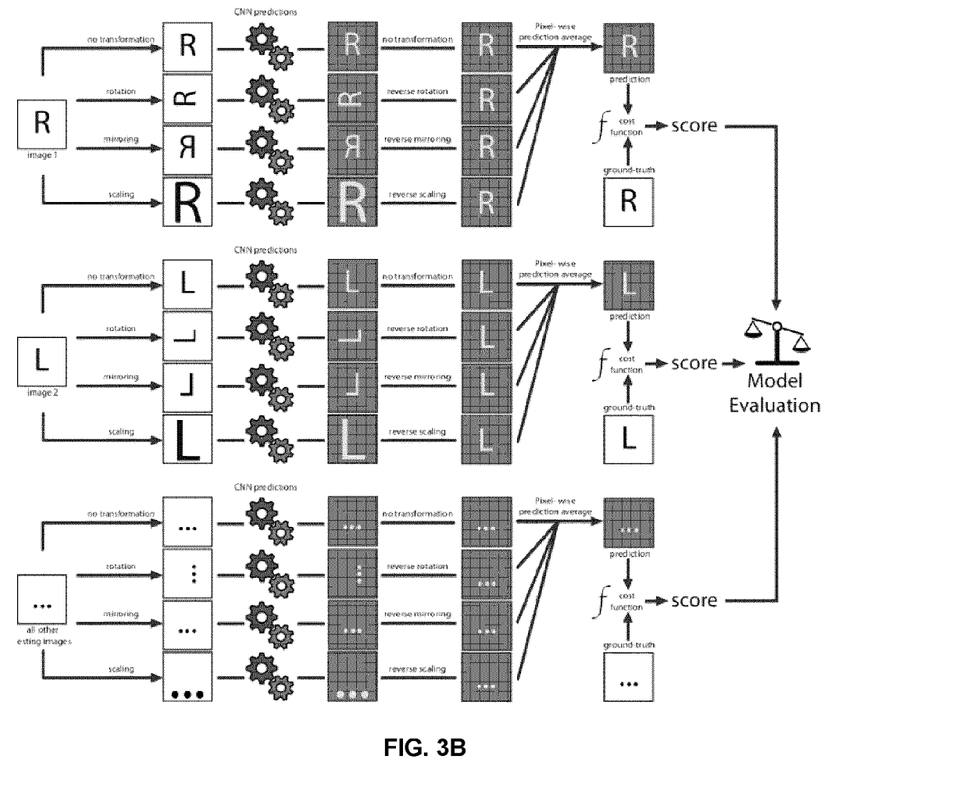
FIG. 3B illustrates an improved convolutional neural network model evaluation workflow including test time augmentation for semantic segmentation.

In stark contrast, FIG. 3B demonstrates an example embodiment in which test time augmentation is employed during the testing phase. As shown in the figure, in one example implementation, one or more sets of multiparametric MR images (e.g. each image of at least one set of multiparametric images associated with a patient, optionally all multiparametric images associated with all slices) is processed according to a series of transformations to generate additionally transformed images to be processed by the neural network (in the figure, each "image" L, R, etc. is intended to represent a set of MPA-MR images). The originating multiparametric image set is modified in such a way to preserve the underlying "meaning" of the image (for example being rotated or stretched). Each modified multiparametric image set, as well as the original multiparametric image set, is then processed by the network and its prediction task is computed.

Test time augmentation may be beneficial in increasing the robustness of the model, especially when limited testing data is available. According to the present example embodiment, test time augmentation is employed in a post-training manner—i.e. during the testing and deployment phases, as opposed to during the training phase. Accordingly, test time augmentation does not influence the network learned parameters, but it useful in improving the overall robustness by running predictions on the same image multiple times before averaging the results.

Figure 3C:
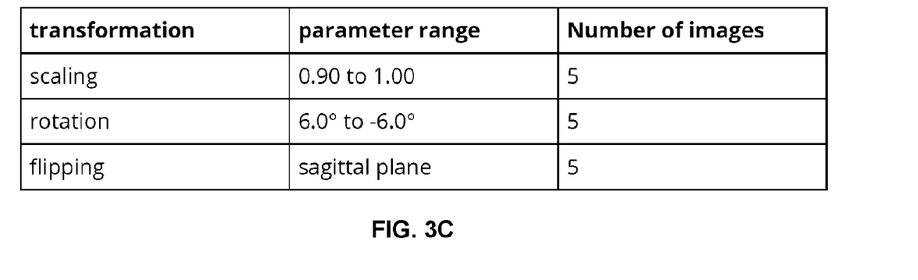
FIG. 3C is a table showing three different example types of transformations that are applied to the original images according to an example test time augmentation method. In the present example implementation, each type of transformation is applied multiple times with parameters randomized within a specific range.

Example transformations for use when performing test time augmentation include, but are not limited to, scaling, rotations, and flipping. For example, one undistorted (unmodified; transformed) image may be combined with n (e.g. 15) distorted (unmodified; transformed) images for a total of n+1 (e.g. 16) images. FIG. 3C provides some non-limiting examples of transformations that may be employed when performing test time augmentation, where each image may be optionally distorted by a random amount within the range specified in the table.

In convention approaches that generate a simple global binary classification of an image as being cancerous or noncancerous, the outputs of the neural network for different augmented multiparametric image sets could simply be combined to generate a final classification in the absence of further processing. However, in the present example embodiments in which the output is a cancer prediction map with per-pixel classification of an image (e.g. as cancerous or noncancerous), further processing of the prediction maps corresponding to the various augmented image sets would need to be performed before they could be combined. In particular, as shown in FIG. 3B, the prediction map associated with each multiparametric image set is rectified by undergoing the inverse of the transformation, and the rectified prediction maps and the unrectified prediction map corresponding to the untransformed image are combined (e.g. averaged) on a per-pixel basis to generate a composite prediction map.

As shown in FIG. 3B, when test time augmentation is employed during the testing phase, the composite prediction map may be compared to the ground truth data, on a per pixel basis, comparing the predicted pixel class with the expected labels based on the ground truth images. The model may be evaluated, for example, by computing and combining a plurality of cost functions, where each cost function is computed based on the per-pixel comparison of a composite prediction map to its associated ground truth image.

It will be understood that while FIG. 3B demonstrates the use of test time augmentation during the testing phase, when the predictions are compared to ground truths, the example augmentation methods described herein may also be employed to generate prediction maps in the deployment phase, based on multiparametric images associated with patients for which ground truth data is not available.

Figure 4:
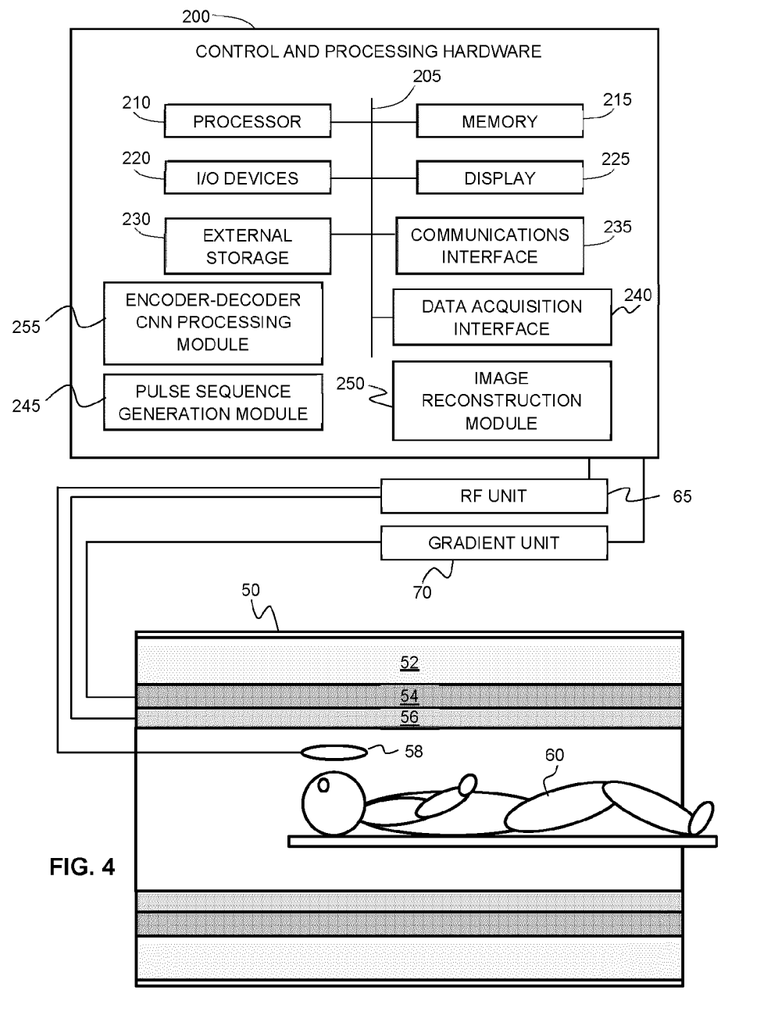
FIG. 4 is an example of a system for generating cancer prediction maps from multiparametric MR images using an encoder-decoder based convolutional neural network.

Referring now to FIG. 4, an example system is illustrated for performing multiparametric MRI and per-pixel image classification using an encoder-decoder convolutional neural network according to the example methods described above. The example system includes a magnetic resonance scanner 50 that employs a main magnet 52 to produce a main magnetic field B0, which generates a polarization in a patient 60 or the examined subject. The example system includes gradient coils 54 for generating magnetic field gradients. A receive coil 58 detects radio frequency (RF) signals from patient 60. The receive coil 58 can also be used as a transmission coil for the generation of RF pulses. Alternatively, a body coil 56 may be employed to radiate and/or detect RF pulses. The RF pulses are generated by an RF unit 65, and the magnetic field gradients are generated by a gradient unit 70.

It will be understood that the magnetic resonance system can have additional units or components that are not shown for clarity, such as, but not limited to, additional control or input devices, and additional sensing devices, such as devices for cardiac and/or respiratory gating. Furthermore, the various units can be realized other than in the depicted separation of the individual units. It is possible that the different components are assembled into units or that different units are combined with one another. Various units (depicted as functional units) can be designed as hardware, software or a combination of hardware and software.

In the example system shown in FIG. 5, a control and processing hardware 200 controls the MRI scanner to generate RF pulses according to a suitable pulse sequence. The control and processing hardware 200 is interfaced with the MRI scanner 50 for controlling the acquisition of the received MRI signals. The control and processing hardware 200 acquires the received MRI signals from the RF unit 65 and processes the MRI signals according to the methods described herein in order to perform magnetic resonance imaging, generate multiparametric MR image data, and processing the multiparametric MR image data in order to generate a cancer prediction map.

The control and processing hardware 200 may be programmed with a set of instructions which when executed in the processor causes the system to perform one or more methods described in the present disclosure. For example, as shown in FIG. 5, control and processing hardware 200 may be programmed with instructions in the form of a set of executable image processing modules, such as, but not limited to, a pulse sequence generation module 245, an image reconstruction module 250, and encoder-decoder convolutional neural network (CNN) processing module 255. The pulse sequence generation module 245 may be implemented using algorithms known to those skilled in the art for pulse sequence generation, such as those described above.

During MRI scanning, RF data is received from the RF coils 56 and/or 58. The pulse sequence generation module 245 establishes the sequence of RF pulses and magnetic field gradients depending on the desired imaging sequence, MR signals responsively emitted by the patient and detected by the coils 56 and/or 58 are acquired. The image reconstruction module 245 processes the acquired MRI signals to perform image reconstruction and MRI image generation. The convolutional neural network processing module generates one or more cancer prediction maps according to the example method shown in FIG. 1A, or variations thereof.

The control and processing hardware 200 may include, for example, one or more processors 210, memory 215, a system bus 205, one or more input/output devices 220, and a plurality of optional additional devices such as communications interface 235, data acquisition interface 240, display 225, and external storage 230.

It is to be understood that the example system shown in FIG. 5 is illustrative of a non-limiting example embodiment and is not intended to be limited to the components shown. For example, the system may include one or more additional processors and memory devices. Furthermore, one or more components of control and processing hardware 200 may be provided as an external component that is interfaced to a processing device. For example, the algorithms described in the present disclosure may be implemented in the MRI reconstruction hardware (as a component of an MRI system), or on an advanced image processing station that may be provided separately from the main MRI system for advanced image post processing. The latter may be provided, for example, as servers with multiple CPU processors and independent data storage/processing capabilities that provide thin or thick client solutions to process one or multiple series of MRI image datasets. This is done to produce post-processing outputs of advanced parameters or features typically derived from one or a combination of MRI datasets. Examples of such post-processed outputs, in addition to those provided by the present example methods, include quantitative imaging (blood flow, vessel permeability, heart function), image fusion visualization between multiple contrasts.

Some aspects of the present disclosure can be embodied, at least in part, in software, which, when executed on a computing system, configures the computing system as a specialty-purpose computing system that is capable of performing the signal processing and noise reduction methods disclosed herein, or variations thereof. That is, the techniques can be carried out in a computer system or other data processing system in response to its processor, such as a microprocessor, CPU or GPU, executing sequences of instructions contained in a memory, such as ROM, volatile RAM, non-volatile memory, cache, magnetic and optical disks, cloud processors, or other remote storage devices. Further, the instructions can be downloaded into a computing device over a data network, such as in a form of a compiled and linked version. Alternatively, the logic to perform the processes as discussed above could be implemented in additional computer and/or machine-readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine-readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), network attached storage, cloud storage, among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

While some of the example embodiments described herein pertain to the use of encoder-decoder convolutional neural networks for the per-pixel classification of multiparametric MR prostate images for the detection of prostate cancer (prostate adenocarcinoma), it will be understood that the example network architectures and methods described herein may be employed for the detection of cancer in a wide range of anatomical regions and organs. For example, in some non-limiting example alternative embodiments, the systems and methods described herein may be employed for the detection of cancer in organs such as the liver and pancreas.

EXAMPLES

The following examples are presented to enable those skilled in the art to understand and to practice embodiments of the present disclosure. They should not be considered as a limitation on the scope of the disclosure, but merely as being illustrative and representative thereof.

Example 1: Training Set Labelling for Prostate Cancer

Figure 5A:
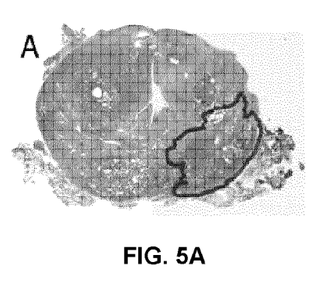
FIGS. 5A-5C show (A) an example of a histopathology section from prostatectomy sample with its matching T2w MR (magnetic resonance) image (B), while (C) shows the overlay between the two images.
Figure 5B:
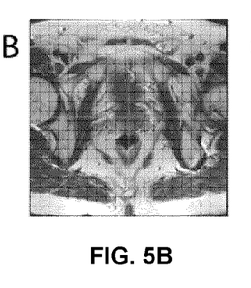
Figure 5C:
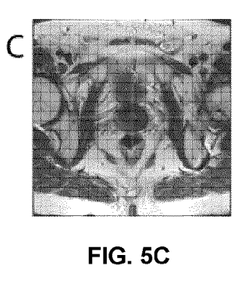

The present example describes a non-limiting method of performing training set labelling for multiparametric MR prostate images. Patients referred for clinically indicated multiparametric MRI who subsequently underwent radical prostatectomy were prospectively recruited. Multiparametric MR Images were collected for each subject are were represented by a series of s slices, each with dimensions 512×512 and 3 channels (c: T2w, ADC, Ktrans). Specimens from the patients were grossed and the corresponding slides annotated by genitourinary pathologists blinded to the MRI data. Annotated slides outlining the tumor were scanned and digitally reconstructed to create pseudo-wholemount specimens, as shown in FIGS. 5A-5C). Clinically significant cancer (defined as Gleason score 3+4 or greater) and visibility on MRI with a minimum diameter 0.5 cm in the axial plane correlated the histopathological sections with the MR images and manually delineated the tumor margins on either T2w or ADC maps, depending on tumor location, according to PIRADS 2.

Example 2: Example Pretraining Method

In the present example implementation, the ImageNet dataset (Deng et al. 2009) was used for the source task to pretrain the convolutional neural network. This data consists of approximately 14 million RGB images of everyday objects which are sorted classes based on what object is present in the image (e.g. dog, cat, car, etc.) The network is then trained to classify the images into the appropriate class. Although the images may not be similar to prostate MRI images, the advantage of this approach is that the network is not longer randomly initiate but low-level features and filters already learned using the Imagenet dataset.

Example 3: Example Training Method and Constraints

The following example provides an example method of training an encoder-decoder convolutional neural network. In the present example implementation, the training multiparametric MR images were cropped around the prostate region, and the images thus had a non-fixed input size. A batch size of one is therefore used.

The objective function shown below (equation 1) used to train the network is based on the cost function proposed by Milletari, Navab, and Ahmadi (2016):

$$\text{Cost} = \frac{\sum_{i=1}^{n} \left( \hat{p}^{(i)} \cdot \hat{y}^{(i)} + \hat{p}_c^{(i)} \cdot y_c^{(i)} \right)}{\sum_{i=1}^{n} \left( \hat{p}^{(i)} \cdot \hat{p}^{(i)} + y^{(i)} \cdot y^{(i)} + \hat{p}_c^{(i)} \cdot \hat{p}_c^{(i)} + y_c^{(i)} \cdot y_c^{(i)} \right)}, \quad (1)$$

where the c subscript indicates the complement: $\hat{p}_c^{(i)}=1-\hat{p}^{(i)}$ and $y_c^{(i)}=1-y^{(i)}$. The cost function is modified so that it would not simply be zero for slices without cancerous pixels.

In the present example implementation, training was performed with the ADAM optimizer (Kingma and Ba 2014), which is available in Tensorflow machine learning framework (Abadi et al. 2016). The learning rate and beta1 parameters of the algorithm were set to $6\times10^{-6}$ and 0.99 respectively. All other parameters are set to their default values.

Example 4: Results

The present example demonstrates the ability to provide clear and accurate cancer prediction maps, with pixelwise resolution, based on clinical samples. The predictions were generated by a model having an architecture based on that shown in FIG. 2 and trained according to the methods described above, with testing performed using test time augmentation.

Figures 6A, 6B, 6C, 6D, 6E, 6F, 6G, 6H:
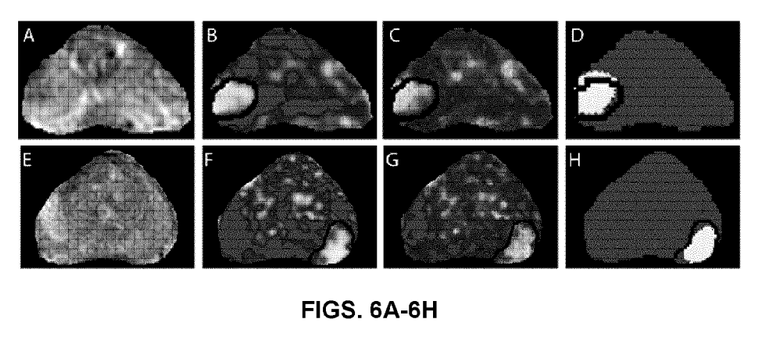

FIGS. 6A-6E show a series of prostate images and associated cancer prediction maps. Light gray regions indicate cancer predicted voxels, dark gray regions are non-cancer predictions for the different models tested. FIG. 6A shows an original prostate image from the first subject, slice 18 and FIG. 6E shows an image from the second subject slice 13, both shown using channel T2w. Voxel values of the regions outside the prostate are set to 0. FIGS. 6B and 6F show the cancer segmentation using a Logistic Regression classifier; FIGS. 6C and 6G show the cancer segmentation for a Random Forest classifier; and FIGS. 6D and 6H show results from the CNN model with TTA and supervised transfer learning.

It can be seen from the present example that the anisotropic encoder-decoder convolutional neural network is able to identify the location of the tumor with performing F1 scores.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

Abadi, Martin, Ashish Agarwal, Paul Barham, Eugene Brevdo, Zhifeng Chen, Craig Citro, Greg S. Corrado, et al. 2016. "TensorFlow: Large-Scale Machine Learning on Heterogeneous Distributed Systems." *arXiv* [*cs.DC*]. arXiv. http://arxiv.org/abs/1603.04467.

Deng, J., W. Dong, R. Socher, L. Li, Kai Li, and Li Fei-Fei. 2009. "ImageNet: A Large-Scale Hierarchical Image Database." In 2009 *IEEE Conference on Computer Vision and Pattern Recognition*, 248-55.

Dieleman, Sander, Jeffrey De Fauw, and Koray Kavukcuoglu. 2016. "Exploiting Cyclic Symmetry in Convolutional Neural Networks." *arXiv* [*cs.LG*]. arXiv. http://arxiv.org/abs/1602.02660.

Dumoulin, Vincent, and Francesco Visin. 2016. "A Guide to Convolution Arithmetic for Deep Learning." arXiv [stat.ML]. arXiv. http://arxiv.org/abs/1603.07285.

Garcia-Reyes, Kirema, Niccolò, M. Passoni, Mark L. Palmeri, Christopher R. Kauffman, Kingshuk Roy Choudhury, Thomas J. Polascik, and Rajan T. Gupta. 2015. "Detection of Prostate Cancer with Multiparametric MRI (mpMRI): Effect of Dedicated Reader Education on Accuracy and Confidence of Index and Anterior Cancer Diagnosis." *Abdominal Imaging* 40 (1): 134-42.

Giannini, Valentina, Simone Mazzetti, Enrico Armando, Silvia Carabalona, Filippo Russo, Alessandro Giacobbe, Giovanni Muto, and Daniele Regge. 2017. "Multiparametric Magnetic Resonance Imaging of the Prostate with Computer-Aided Detection: Experienced Observer Performance Study." *European Radiology* 27 (10): 4200-4208.

Hambrock, Thomas, and B. MBCh. 2013. "Prostate Cancer: Computer-Aided Diagnosis with Multiparametric 3-T MR Imaging—Effect on Observer Performance1." *Radiology* 266 (2). https://doi.org/He, Kaiming, Xiangyu Zhang, Shaoqing Ren, and Jian Sun. 2015. "Deep Residual Learning for Image Recognition." *arXiv* [*cs.CV*]. arXiv. http://arxiv.org/abs/1512.03385.

Hua, Kai-Lung, Che-Hao Hsu, Shintami Chusnul Hidayati, Wen-Huang Cheng, and Yu-Jen Chen. 2015. "Computer-Aided Classification of Lung Nodules on Computed Tomography Images via Deep Learning Technique." *Onco Targets and Therapy* 8 (August): 2015-22.

Kingma, Diederik P., and Jimmy Ba. 2014. "Adam: A Method for Stochastic Optimization." *arXiv* [*cs.LG*]. arXiv. http://arxiv.org/abs/1412.6980.

Lakhani, Paras, and Baskaran Sundaram. 2017. "Deep Learning at Chest Radiography: Automated Classification of Pulmonary Tuberculosis by Using Convolutional Neural Networks." *Radiology* 284 (2): 574-82.

Le, Minh Hung, Jingyu Chen, Liang Wang, Zhiwei Wang, Wenyu Liu, Kwang-Ting Tim Cheng, and Xin Yang. 2017. "Automated Diagnosis of Prostate Cancer in Multi-Parametric MRI Based on Multimodal Convolutional Neural Networks." *Physics in Medicine and Biology* 62 (16): 6497-6514.

Milletari, F., N. Navab, and S. Ahmadi. 2016. "V-Net: Fully Convolutional Neural Networks for Volumetric Medical Image Segmentation." In 2016 *Fourth International Conference on* 3D *Vision* (3DV), 565-71.

Muller, Berrend G., Joanna H. Shih, Sandeep Sankineni, Jamie Marko, Soroush Rais-Bahrami, Arvin Koruthu George, Jean J. M. C. H. de la Rosette, et al. 2015. "Prostate Cancer: Interobserver Agreement and Accuracy with the Revised Prostate Imaging Reporting and Data System at Multiparametric MR Imaging." *Radiology* 277 (3): 741-50.

Pereira, Sergio, Adriano Pinto, Victor Alves, and Carlos A. Silva. 2016. "Brain Tumor Segmentation Using Convolutional Neural Networks in MRI Images." *IEEE Transactions on Medical Imaging* 35 (5): 1240-51.

Roehrborn, Claus G., and Libby K. Black. 2011. "The Economic Burden of Prostate Cancer." *BJU International* 108 (6): 806-13.

Rosenkrantz, Andrew B., Luke A. Ginocchio, Daniel Cornfeld, Adam T. Froemming, Rajan T. Gupta, Baris Turkbey, Antonio C. Westphalen, James S. Babb, and Daniel J. Margolis. 2016. "Interobserver Reproducibility of the PI-RADS Version 2 Lexicon: A Multicenter Study of Six Experienced Prostate Radiologists." *Radiology* 280 (3): 793-804.

Sanyal, C., A. G. Aprikian, S. Chevalier, F. L. Cury, and A. Dragomir. 2013. "Direct Cost for Initial Management of Prostate Cancer: A Systematic Review." *Current Oncology* 20 (6): e522-31.

Sermanet, Pierre, David Eigen, Xiang Zhang, Michael Mathieu, Rob Fergus, and Yann LeCun. 2013. "OverFeat: Integrated Recognition, Localization and Detection Using Convolutional Networks." arXiv [cs.CV]. arXiv. http://arxiv.org/abs/1312.6229.

Shelhamer, Evan, Jonathan Long, and Trevor Darrell. 2017. "Fully Convolutional Networks for Semantic Segmentation." *IEEE Transactions on Pattern Analysis and Machine Intelligence* 39 (4): 640-51.

Shi, Wenzhe, Jose Caballero, Lucas Theis, Ferenc Huszar, Andrew Aitken, Christian Ledig, and Zehan Wang. 2016. "Is the Deconvolution Layer the Same as a Convolutional Layer?" arXiv [cs.CV]. arXiv. http://arxiv.org/abs/1609.07009.

Simonyan, Karen, and Andrew Zisserman. 2014. "Very Deep Convolutional Networks for Large-Scale Image Recognition." arXiv [cs.CV]. arXiv. http://arxiv.org/abs/1409.1556.

Torre, Lindsey A., Freddie Bray, Rebecca L. Siegel, Jacques Ferlay, Joannie Lortet-Tieulent, and Ahmedin Jemal. 2015. "Global Cancer Statistics, 2012." *CA: A Cancer Journal for Clinicians* 65 (2): 87-108.

Weinreb, Jeffrey C., Jelle O. Barentsz, Peter L. Choyke, Francois Comud, Masoom A. Haider, Katarzyna J. Macura, Daniel Margolis, et al. 2016. "PI-RADS Prostate Imaging—Reporting and Data System: 2015, Version 2." *European Urology* 69 (1): 16-40.

Yang, Xin, Chaoyue Liu, Zhiwei Wang, Jun Yang, Hung Le Min, Liang Wang, and Kwang-Ting Tim Cheng. 2017. "Co-Trained Convolutional Neural Networks for Automated Detection of Prostate Cancer in Multi-Parametric MRI." *Medical Image Analysis* 42 (December): 212-27.

Yosinski, Jason, Jeff Clune, Yoshua Bengio, and Hod Lipson. 2014. "How Transferable Are Features in Deep Neural Networks?" In *Advances in Neural Information Processing Systems* 27, edited by Z. Ghahramani, M. Welling, C. Cortes, N. D. Lawrence, and K. Q. Weinberger, 3320-28. Curran Associates, Inc.

Therefore what is claimed is:

1. A method of implementing a convolutional neural network for generating cancer prediction maps based on processing of multiparametric magnetic resonance images, the method comprising:
    defining an anisotropic encoder-decoder convolutional neural network for processing multiparametric magnetic resonance images, wherein the anisotropic encoder-decoder convolutional neural network is configured such that an output thereof is a pixelated prediction image map, with each pixel of the pixelated prediction image map configured to provide a binary determination of a presence or absence of cancer;
    performing supervised transfer learning to pretrain the anisotropic encoder-decoder convolutional neural network;
    training the anisotropic encoder-decoder convolutional neural network with a plurality of multiparametric magnetic resonance training image sets and respective ground truth training image sets, each multiparametric magnetic resonance training image set corresponding to a given subject and comprising a plurality of multiparametric magnetic resonance image slices; and
    employing test-time-augmentation to test the anisotropic encoder-decoder convolutional neural network with a plurality of multiparametric magnetic resonance test image sets and respective ground truth test image sets;
    wherein test-time-augmentation is performed, when processing a given slice of a multiparametric magnetic resonance test image set, according to the steps of:
        applying a plurality of transformations to the multiparametric magnetic resonance images corresponding to the given slice, thereby obtaining a plurality of transformed multiparametric magnetic resonance images;
        employing the anisotropic encoder-decoder convolutional neural network to generate, for each transformed multiparametric magnetic resonance image, an intermediate cancer prediction map;
        rectifying each intermediate cancer prediction map by applying a respective inverse transformation, thereby obtaining a plurality of rectified intermediate cancer prediction maps; and
        combining the plurality of rectified intermediate cancer prediction maps to generate a composite cancer prediction map.

2. The method according to claim 1 further comprising deploying the anisotropic encoder-decoder convolutional neural network to process a multiparametric magnetic resonance image set from a subject and generate a plurality of cancer prediction maps for the subject.

3. The method according to claim 1 wherein the encoder portion of the anisotropic encoder-decoder convolutional neural network includes a greater number of layers than the decoder portion of the anisotropic encoder-decoder convolutional neural network.

4. The method according to claim 1 wherein the anisotropic encoder-decoder convolutional neural network includes at least one short-cut connection.

5. The method according to claim 1 wherein the encoder portion of the anisotropic encoder-decoder convolutional neural network includes three or fewer convolution blocks, each convolution block comprising two convolution layers and a maxpool layer.

6. The method according to claim 1 wherein the decoder portion of the anisotropic encoder-decoder convolutional neural network comprises three or fewer transposed convolution layers.

7. The method according to claim 1 wherein the composite cancer prediction map is generated with a 1×1 pixel mapping relationship to the multiparametric magnetic resonance images.

8. The method according to claim 1 wherein the multiparametric magnetic resonance training image sets and the multiparametric magnetic resonance test image sets are multiparametric magnetic resonance image sets of the prostate.

9. The method according to claim 1 wherein the multiparametric magnetic resonance training image sets and the multiparametric magnetic resonance test image sets are multiparametric magnetic resonance image sets of the pancreas.

10. The method according to claim 1 wherein the multiparametric magnetic resonance training image sets and the multiparametric magnetic resonance test image sets are obtained from less than 100 subjects.

11. The method according to claim 1 wherein the multiparametric magnetic resonance training image sets and the multiparametric magnetic resonance test image sets are obtained from less than 50 subjects.

12. The method according to claim 1 wherein the multiparametric magnetic resonance training image sets and the multiparametric magnetic resonance test image sets are obtained from less than 20 subjects.

13. A method of employing an anisotropic encoder-decoder convolutional neural network to generate cancer prediction maps based on processing of a multiparametric magnetic resonance image set associated with a subject, the anisotropic encoder-decoder convolutional neural network being configured such that an output thereof is a pixelated prediction image map, with each pixel of the pixelated prediction image map configured to provide a binary determination of a presence or absence of cancer;

the method comprising employing test-time-augmentation to process the multiparametric magnetic resonance image set via the anisotropic encoder-decoder convolutional neural network;

wherein test-time-augmentation is performed, when processing a given slice of the multiparametric magnetic resonance image set, according to the steps of:

applying a plurality of transformations to the multiparametric magnetic resonance images corresponding to the given slice, thereby obtaining a plurality of transformed multiparametric magnetic resonance images;

employing the anisotropic encoder-decoder convolutional neural network to generate, for each transformed multiparametric magnetic resonance image, an intermediate cancer prediction map;

rectifying each intermediate cancer prediction map by applying a respective inverse transformation, thereby obtaining a plurality of rectified intermediate cancer prediction maps; and combining the plurality of rectified intermediate cancer prediction maps to generate a composite cancer prediction map.

14. A system for processing multiparametric magnetic resonance images for cancer segmentation, the system comprising:

processing circuitry comprising at least one processor and associated memory, wherein the memory stores instructions executable by the at least one processor for performing operations comprising:

employing test-time-augmentation to process a multiparametric magnetic resonance image set via an anisotropic encoder-decoder convolutional neural network, the anisotropic encoder-decoder convolutional neural network being configured such that an output thereof is a pixelated prediction image map, with each pixel of the pixelated prediction image map configured to provide a binary determination of a presence or absence of cancer;

wherein test-time-augmentation is performed, when processing a given slice of the multiparametric magnetic resonance image set, according to the steps of:

applying a plurality of transformations to the multiparametric magnetic resonance images corresponding to the given slice, thereby obtaining a plurality of transformed multiparametric magnetic resonance images;

employing the anisotropic encoder-decoder convolutional neural network to generate, for each transformed multiparametric magnetic resonance image, an intermediate cancer prediction map;

rectifying each intermediate cancer prediction map by applying a respective inverse transformation, thereby obtaining a plurality of rectified intermediate cancer prediction maps; and combining the plurality of rectified intermediate cancer prediction maps to generate a composite cancer prediction map.

15. The system according to claim 14 wherein the processing circuitry is configured such that the encoder portion of the anisotropic encoder-decoder convolutional neural network includes a greater number of layers than the decoder portion of the anisotropic encoder-decoder convolutional neural network.

16. The system according to claim 14 wherein the processing circuitry is configured such that the anisotropic encoder-decoder convolutional neural network includes at least one short-cut connection.

17. The system according to claim 14 wherein the processing circuitry is configured such that the encoder portion of the anisotropic encoder-decoder convolutional neural network includes three or fewer convolution blocks, each convolution block comprising two convolution layers and a maxpool layer.

18. The system according to claim 14 wherein the processing circuitry is configured such that the decoder portion of the anisotropic encoder-decoder convolutional neural network comprises three or fewer transposed convolution layers.

19. The system according to claim 14 wherein the processing circuitry is configured such that the composite cancer prediction map is generated with a 1×1 pixel mapping relationship to the multiparametric magnetic resonance images.

20. The system according to claim 14 wherein the processing circuitry is configured such that the multiparametric magnetic resonance training image sets and the multiparametric magnetic resonance test image sets are multiparametric magnetic resonance image sets of the prostate.

21. The system according to claim 14 wherein the processing circuitry is configured such that the multiparametric magnetic resonance training image sets and the multiparametric magnetic resonance test image sets are multiparametric magnetic resonance image sets of the pancreas.

* * * * *